United States Patent [19]

Evans et al.

[11] 4,082,771

[45] Apr. 4, 1978

[54] ACYLAMINO DERIVATIVES

[75] Inventors: Delme Evans, Chalfont St. Peter; Michael Ralph John Jolley, Camberley; William James Ross, Lightwater; Brian Picton Swann, Camberley, all of England

[73] Assignee: Lilly Industries Limited, London, England

[21] Appl. No.: 691,961

[22] Filed: Jun. 1, 1976

[30] Foreign Application Priority Data

Jun. 5, 1975 United Kingdom ............... 24223/75

[51] Int. Cl.$^2$ ...................... C07D 333/24; A01N 9/00
[52] U.S. Cl. ........................... 260/332.2 R; 260/347.3; 424/275; 424/285
[58] Field of Search ................. 260/332.2 R, 332.3 R

[56] References Cited

U.S. PATENT DOCUMENTS 3,506,678  4/1970  Hoff et al. .......................... 260/332.2

FOREIGN PATENT DOCUMENTS 39-5637  4/1964  Japan ................................ 260/332.2

Primary Examiner—Alan M. Siegel
Attorney, Agent, or Firm—Nancy J. Harrison; Everet F. Smith

[57] ABSTRACT

Acylamino heteroaryl compounds in which the heteroaryl nucleus is a 5-membered ring containing a single heteroatom, which may be oxygen, or sulphur, methods of making the compounds and pharmaceutical formulations containing the compounds. The compounds have anti-allergy activity.

4 Claims, No Drawings

ACYLAMINO DERIVATIVES

This invention relates to heterocyclic chemical compounds and more particularly to certain novel 5-membered heterocyclics substituted by an acylamino group which possess utility in the treatment of immediate hypersensitivity conditions and/or which are useful as intermediates in preparing such active compounds. The invention also includes processes for preparing the compounds of the invention. Furthermore, the invention includes within its scope pharmaceutical compositions containing the pharmacologically active compounds and methods of treatment of animals, including humans, comprising administering thereto an effective dose of the compound or compounds or of pharmaceutical compositions comprising the active compound or compounds.

Certain acylamino thiophenes have been previously described in Japanese Patent Specification Nos. 9045058 and 4016861, Belgian Patent Specification No. 767244, Dutch Patent Specification No. 7106324 and French Patent Specification No. 1,585,075. However, those thiophenes are described as being intermediates or as having utilities, e.g. herbicidal, antiinflammatory, antipyretic, etc., quite divorced from the anti-allergic activity which the novel compounds of the invention have been found to possess.

According to the present invention there is provided a novel heteroaryl derivative of formula (I) :

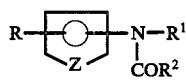
(I)

wherein Z represents an oxygen or sulphur atom; R is hydrogen, $C_{1-4}$ alkyl or phenyl optionally substituted by halogen, trifluoromethyl or $C_{1-3}$ alkoxy; $R^1$ is $C_{1-7}$ alkyl, $C_{3-6}$ alkenyl, $C_{3-6}$ alkynyl or benzyl optionally substituted by halogen or nitro; and $R^2$ is $C_{1-7}$ alkyl, $C_{3-10}$ cycloalkyl, phenyl or benzyl; provided that when Z is —S— and R is hydrogen, $R^2$ cannot be methyl when $R^1$ is methyl, ethyl or benzyl.

When Z is oxygen the compounds of formula (I) are furans, when Z is sulphur the compounds of formula (I) are thiophenes.

The acylamino group —$NR^1COR^2$ may be attached at the 2- or 3-position of the heteroaryl nucleus.

The term "$C_{1-7}$ alkyl" as used herein means a straight or branched chain alkyl group containing from 1 to 7 carbon atoms such as methyl, ethyl, isopropyl, n-butyl, s-butyl, isobutyl, t-butyl, n-amyl, s-amyl, n-hexyl, 2-ethylbutyl, 4-methylamyl or heptyl. The term "$C_{3-6}$ alkynyl" is used herein to indicate an alicyclic hydrocarbon group having 3 to 6 carbon atoms which contains a —C≡C— group. However, it should be noted that the —C≡C— group cannot be directly adjacent the nitrogen atom of the acylamino group, similarly a —C═C— group cannot be directly adjacent said nitrogen atom in a $C_{3-6}$ alkenyl group. "$C_{3-10}$ cycloalkyl" means a saturated ring having 3 to 10 carbon atoms in the ring such as cyclopropyl, cyclobutyl, cyclopentyl, cyclooctyl or adamantyl.

Preferred classes of compounds falling within the scope of the heterocyclic derivatives of formula (I) above are those having one or more of the following characteristics:

(A) Z is O,
(B) Z is S,
(C) $R^1$ is $C_{1-7}$ alkyl or $C_{3-6}$ alkenyl,
(D) $R^1$ is $C_{2-6}$ alkyl, $C_{3-6}$ alkenyl or benzyl optionally substituted by halogen,
(E) $R^1$ is $C_{3-6}$ alkyl, $C_{3-4}$ alkenyl or benzyl,
(F) $R^2$ is $C_{1-7}$ alkyl or benzyl,
(G) $R^2$ is $C_{1-7}$ alkyl, $C_{3-5}$ cycloalkyl or phenyl,
(H) $R^2$ is $C_{1-4}$ alkyl,
(I) $R^2$ is $C_{1-4}$ alkyl, $C_{3-5}$ cycloalkyl, or phenyl,
(J) the heteroaryl nucleus is singly substituted by $C_{1-4}$ alkyl or phenyl,
(K) the acylamino group —$NR^1COR^2$ is present at the 2- or 3- position of the heteroaryl nucleus and heteroaryl nucleus is substituted at the 5-position,
(L) the heteroaryl nucleus is unsubstituted.

The compounds of formula (I) may be prepared by
(a) alkylating an acyl derivative of formula:

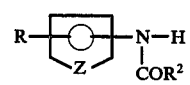
(IX)

where R, $R^2$ and Z are as defined above;
(b) acylating a compound of formula:

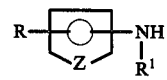
(X)

where R, Z and $R^1$ are as defined above; or
(c) decarboxylating the corresponding acid of formula:

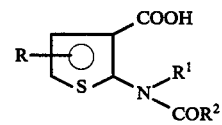
(XI)

where R, $R^1$ and $R^2$ are as defined above so as to form a compound of formula:

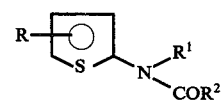
(XII)

When Z is O, method (a) is highly preferred since aminofurans are unstable, being particularly susceptible to air-oxidation. Indeed, their instability is such that method (b) can only be adopted for aminofurans which are stabilised by an electron withdrawing entity in the ring such as an ester group. Aminothiophenes tend to be more stable; however, even those amines should be acylated only in the form of their salts, e.g. their hydrochloride and hydrochloride/stannic chloride salts.

Compounds of formula (IX) can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula $R^1X$ where X is a reactive atom such as a halogen atom, preferably iodine, or a reactive group such as an alkyl sulphate group.

Of course, alkylating agents and alkylating reaction conditions other than those specified above can be utilised, the nature of these being readily apparent to those acquainted with the art.

The acylation of the compound of formula (X) may be carried out with an acid halide having the formula $R^2CO-X^1$ wherein $X^1$ is chlorine or bromine and $R^2$ is as defined above, in the presence of a proton acceptor, such as pyridine or triethylamine, in an inert solvent, such as benzene. The acylation may also be carried out by heating the amino derivative of formula (X) with a suitable acid anhydride, $(R^2CO)_2O$, in an inert solvent.

Those skilled in the art will immediately appreciate that a wide variety of other acylating conditions can be used (see, for example, "The Chemistry of Amides" 1971 by A. J. Beckwith; "Survey of Organic Synthesis", 1970 by Buehler and Pearson; "Organic Functional Group Preparations" 1968 by Sandler and Karo; "Reagents for Organic Synthesis" 1968 by Fieser and Fieser etc.).

The decarboxylation of the acid of formula (XI) can be accomplished by heating the acid alone or in the presence of a solvent with a high boiling point (e.g. collidine), preferably under an inert gas atmosphere.

Compounds of formula (IX) in which Z is oxygen can be prepared using the following reaction scheme:

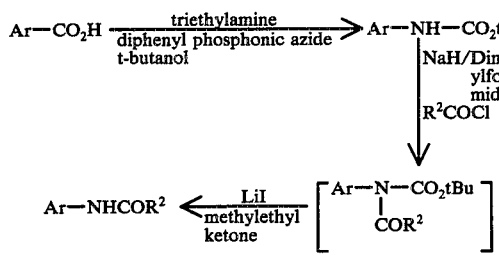

where Ar indicates the optionally substituted furyl moiety.

Acids of formula $ArCO_2H$ are known compounds or can be prepared by literature methods from readily available starting materials, see for example *Journal of the Chemical Society*, Perkin I (1973), 1766.

Compounds of formula (IX) in which Z is sulphur can be prepared by the above procedure using as starting material the appropriate S acids, which are known in the literature, see Compaigne, *Journal of the American Chemical Socieity*, 1951, 73, 3812.

Alternatively, the thiophene amides can be prepared by the decarboxylation of the correspondingNH amides of formula:

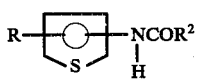
(XVI)

where one of the available positions, preferably a position adjacent the acylamino group, in the thiophene nucleus is substituted by an ester or acid group. Compounds of formula (XVI) may be prepared from the corresponding amines or salts of formula:

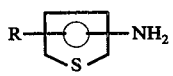
(XVII)

or their salts by acylation. (*J. Prakt. Chem.* 315, 539 (1973))

Preparation of amines of the type (XVII) is described in *Chemische Berichte*, 1966, 99, 94. It is to be noted that such amines are stablised by the electron-withdrawing ester group.

Intermediates of formula (IX) where Z is O are novel and are provided in a further aspect of the invention.

Compounds of formula (I) have been shown to be useful in the prophylactic and therapeutic treatment of immediate hypersensitivity diseases including asthma and in the alleviation of status asthmaticus. The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 0.5 to 300 mg/kg per day, preferably 0.5 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as second tablets, at least one fraction such as a half or a quarter of a severable unit is required for a single therapeutic administration.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbital, mannitol, propylene glycol, liquid paraffin, white soft paraffin, kaolin, fumed silicon dioxide, microcrystalline cellulose, calcium silicate, silica, polyvinylpyrrolidine, cetostearyl alcohol, starch, modified starches, gum acacia, calcium phosphate, cocoa butter, ethoxylated esters, oil of theobrma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminum, magnesium or calcium stearates, talc or mineral oil.

The invention will now be further illustrated by reference to the following Examples.

EXAMPLE 1 tert-Butyl-2-furyl carbamate

2-Furoic acid (56 g, 0.5 mole) was mixed with triethylamine (70 ml, 0.5 mole) and tert-butylalcohol (100 ml) in 1,2-dichloroethane (300 ml) cooled to 0° C. Diphenylphosphonic azide (108 ml, 0.5 mole) was added gradually with stirring and the clear straw coloured solution gradually heated (oil bath, 100°–110° C). Gassing commenced at 65° C, becoming steady and brisk at 80° C with the temperature of the solution finally rising to 85° C. After 4 hours gassing was complete and the brownish solution was poured onto ice/water. The organic phase was separated and washed successively with N/10 hydrochloric acid solution, then saturated sodium bicarbonate solution. The washed organic phase was evaporated (rotary) to give a brownish oil which readily crystallised. The product recrystallised from 60/80° C petroleum ether to yield the desired compound as pale yellow crystals (63.4 g) m.p. 96° C.

EXAMPLE 2

N-(n-Butyl)-N-(fur-2-yl)-3-ethylbutanamide

The tert-butylcarbamate from Example 1 (27.5 g, 0.15 mole) was dissolved in dry tetrahydrofuran (75 ml) and added dropwise at 0°–5° C to a suspension of sodium hydride (50% oil dispersion, 7.2 g, ≡ 0.15 mole) in dry tetrahydrofuran (75 ml). When gassing was complete, the mixture was cooled to −10° C and diethylacetylchloride (20 g, 0.15 mole) in dry tetrahydrofuran (30 ml) added dropwise. The temperature was allowed to come to room temperature over a period of 1 hours and the light brown solution poured onto ice/water. After extraction at ph7 with dichloromethane, the organic solvent phase was evaporated (rotary) to give a light brown oil which was dissolved in methyl ethyl ketone (150 ml) and gently refluxed, on a steam bath, with anhydrous lithium iodide (20 g, 0.15 mole) for 2½–3 hours. The brown solution was evaporated (rotary) to remove methyl ethyl ketone, then poured into water and extracted with benzene at pH2. The benzene extract was washed successively with saturated potassium bicarbonate solution, then water and evaporated (rotary) to give a light brown crystalline solid which was recrystallised from benzene/petroleum ether 60/80° C to yield 2-(2′-ethylbutanamido)furan (19.6 g) m.p. 100° C.

This product (18.1 g, 0.1 mole) was then dissolved in dry dimethylformamide (50 ml) and added dropwise with stirring to a suspension of sodium hydride (50% oil dispersion 4.8 g, 0.1 mole) in dry dimethylformamide (75 ml) with cooling to 10° C. After gassing was complete, a butyliodide (19.0 g 0.1 mole) was added dropwise with continued stirring. After warming to room temperature over 1.5–2 hours, the mixture was treated with a few drops of ethanol to destroy any remaining sodium hydride, then poured onto ice/water and extracted into dichloromethane at pH7 by adjustment with a few drops of glacial acetic acid. The organic extract was evaporated (rotary) to give a light brown mobile liquid which was fractionally distilled in vacuo to give the desired compound as a colourless (15.0 g) b.p. 106° C/1 mm.

Analysis: $C_{14}H_{23}NO_2$ req.: C 70.8; H 9.77; N 5.90%. found: C 70.6; H 9.42; N 5.57%.

EXAMPLE 3

N-n-Butyl-N-(fur-2-yl)-2-methylpropanamide

The title compound was prepared by the procedure of Example 2 but using isobutyrylchloride instead of diethyl acetyl chloride. b.p. 92° C/2 mm.

Analysis: $C_{12}H_{19}NO_2$ req.: C 68.9; H 9.15; N 6.69%. found: C 68.7; H 9.32; N 6.52%.

EXAMPLE 4

N-(n-Butyl)-N-(fur-2-yl)acetamide

The title compound was prepared by the procedure of Example 2 but using acetyl chloride and in the final alkylation step, extracting via ether and using n-butyliodide. b.p. 66° C/0.09 mm.

Analysis: $C_{10}H_{15}NO_2$ req.: C 66.3; H 8.34; N 7.73%. found: C 66.2; H 8.12; N 7.65%.

EXAMPLE 5

N-n-Butyl-N-(fur-2-yl)cyclopentanecarboxamide

The title compound was prepared using the procedure of Example 4 but using cyclopentane carboxylic acid chloride. b.p. 96° C/0.15 mm.

Analysis: $C_{14}H_{21}NO_2$ req.: C 71.6; H 9.01; N 5.96%. found: C 71.5; H 9.28; N 6.03%.

EXAMPLE 6

N-n-Butyl-N-(fur-2-yl)cyclohexane carboxamide

The title compound was prepared using the procedure of Example 4 but using cyclohexane carboxylic acid chloride. b.p. 122° C/0.3 mm.

Analysis: $C_{15}H_{23}NO_2$ req.: C 72.4; H 9.31; N 5.63%. found: C 72.3; H 9.13; N 5.52%.

EXAMPLE 7

N-n-Butyl-N-(fur-2-yl)adamantanecarboxamide

The title compound was prepared using the procedure of Example 4 but using 1-adamantane carboxylic acid chloride.

Analysis: $C_{19}H_{27}NO_2$ req.: C 75.7; H 9.03; N 4.65%. found: C 75.9; H 9.25; N 4.92%.

EXAMPLE 8

N-n-Butyl-N-(5-methyl-fur-2-yl)-2-methylpropanamide tert-Butyl-5-methyl-2-furylcarbamate, (mp 80° C, 24 g, 0.12 mole) prepared as in Example 1 from 5-methyl-2-furoic acid was reacted as in Example 2 to give 2-isobutanamido-5-methylfuran (13.4 g) mp 78° C which was then reacted as in Example 4 to give the title compound. b.p. 94° C/0.3 mm.

Analysis: $C_{13}H_{21}NO_2$ req.: C 69.9; H 9.48; N 6.24%. found: C 69.7; H 9.28; N 6.43%.

EXAMPLE 9

N-n-Butyl-N-(5-methyl-fur-2-yl)-3-ethylbutanamide

The title compound was prepared using the procedure of Example 8 but using diethylacetylchloride as the acid chloride. b.p. 102° C/0.1 mm.

Analysis: $C_{15}H_{25}NO_2$ req.: C 71.7; H 10.02; N 5.57%. found: C 71.6; H 10.12; N 5.74%.

EXAMPLE 10

N-n-Butyl-N-(5-methyl-fur-2-yl)cyclopentanecarboxamide

The title compound was prepared using the procedure of Example 8 but using cyclopentancarboxylic acid chloride. b.p. 115° C/0.2 mm.

Analysis: $C_{15}H_{23}NO_2$ req.: C 72.3; H 9.30; N 5.62%. found: C 72.5; H 9.57; N 5.52%.

EXAMPLE 11

N-Methyl-N-(5-methyl-fur-2-yl)cyclopentanecarboxamide

The title compound was prepared using the procedure of Example 10 but using methyl iodide in the final step also with silica gel chromatography (ethylacetate/petrol 60/80° C 1/10v/v as developing solvent). b.p. 150° C/1 mm. (Kugelrohr).

Analysis: $C_{12}H_{17}NO_2$ req.: C 69.6; H 8.28; N 6.77%. found: C 66.8; H 7.71; N 6.37%.

EXAMPLE 12

N-Ethyl-N-(5-methyl-fur-2-yl)cyclopentanecarboxamide

The title compound was prepared using the procedure of Example 11 but using ethyl iodide in the final step. b.p. 150° C/1 mm. (Kugelrohr).

Analysis: $C_{13}H_{19}NO_2$ req.: C 70.6; H 8.67; N 6.34%. found: C 70.4; H 8.47; N 6.18%.

EXAMPLE 13

N-(5-Methyl-fur-2-yl)N-(n-propyl)cyclopentanecarboxamide

The title compound was prepared using the procedure of Example 11 but using 1-iodopropane in the final step. b.p. 150° C/1 mm. (Kugelrohr).

Analysis: $C_{14}H_{21}NO_2$ req.: C 71.6; H 9.01; N 5.96%. found: C 69.5; H 8.85; N 6.26%.

EXAMPLE 14

N-Hexyl-N-(5-methyl-fur-2-yl)cyclopentanecarboxamide

The title compound was prepared using the procedure of Example 10 but using 1-iodohexane in the final step. b.p. 120° C/0.1 mm.

Analysis: $C_{17}H_{27}NO_2$ req.: C 73.6; H 9.81; N 5.05%. found: C 73.8; H 9.53; N 5.20%.

EXAMPLE 15

N-Allyl-N-(5-methyl-fur-2yl)cyclopentanecarboxamide

The title compound was prepared using the procedure of Example 10 but using allyl bromide in the final step. b.p. 94° C/0.08 mm.

Analysis: $C_{14}H_{19}NO_2$ req.: C 72.1; H 8.21; N 6.00%. found: C 72.3; H 8.01; N 6.24%.

EXAMPLE 16

N-Benzyl-N-(5-methyl-fur-2-yl)cyclopentanecarboxamide

The title compound was prepared using the procedure of Example 10 but using benzyl bromide in the final step. b.p. 124° C/0.03 mm.

Analysis: $C_{18}H_{21}NO_2$ req.: C 76.3; H 7.47; N 4.94%. found: C 76.1; H 7.43; N 5.03%.

EXAMPLE 17

N-n-Butyl-N-(5-tert-butyl-fur-2-yl)-2-methylpropanamide

The title compound was prepared using the procedure of Example 8 from 5-tert-butyl-2-furoic acid. b.p. 88° C/0.07 mm.

The product was further purified by silica gel chromatography (using ethyl acetate/petrol 60/80° C 1/10v/v as developing solvent).

Analysis: $C_{16}H_{27}NO_2$ req.: C 72.4; H 10.3; N 5.28%. found: C 72.2; H 10.0; N 5.23%.

EXAMPLE 18

N-(Fur-2-yl)N-propargylcyclohexanecarboxamide

The 2-(cyclohexanecarboxamido)-furan was prepared as in Example 6, m.p. 120° C, and was then reacted with propargyl bromide as in Example 4 to yield the title compound. b.p. 90° C/0.05 mm.

Analysis: $C_{14}H_{17}NO_2$ req.: C 72.7; H 7.41; N 6.06%. found: C 72.6; H 7.48; N 5.82%.

In a similar manner were prepared the following:

EXAMPLE 19

N-Benzyl-N-(fur-2-yl)-acetamide. b.p. 106° C/0.15 mm.

Analysis: $C_{13}H_{13}NO_2$ req.: C 72.5; H 6.09; N 6.50%. found: C 72.6; H 6.06; N 6.48%.

EXAMPLE 20

N-(Fur-2-yl)-N-methylacetamide. b.p. 40° C/0.05 mm.

Analysis: $C_7H_9NO_2$ req.: C 60.4; H 6.51; N 10.1%. found: C 60.2; H 6.37; N 9.97%.

EXAMPLE 21

N-(Fur-2-yl)-N-(4-nitrobenzyl)acetamide. m.p. 54° C

Analysis: $C_{13}H_{12}N_2O_4$ req.: C 60.0; H 4.65; N 10.8%. found: C 59.8; H 4.72; N 10.9%.

EXAMPLE 22

N-Allyl-N-(fur-2-yl)-2-methylpropanamide. b.p. 76° C/1 mm.

Analysis: $C_{11}H_{15}NO_2$ req.: C 68.4; H 7.82; N 7.25%. found: C 68.1; H 7.63; N 7.14%.

EXAMPLE 23

N-Methyl-N-(5-methyl-fur-2-yl)benzamide. b.p. 104° C/0.08 mm.

Analysis: $C_{13}H_{13}NO_2$ req.: C 72.5; H 6.09; N 6.50%. found: C 72.3; H 6.31; N 6.45%.

EXAMPLE 24

N-Allyl-N-(5-methyl-fur-2-yl)benazmide. b.p. 115° C/0.08 mm.

Analysis: $C_{15}H_{15}NO_2$ req.: C 74.7; H 6.27; N 5.81%. found: C 74.9; H 6.47; N 6.06%.

EXAMPLE 25

N-Methyl-N-(5-methyl-fur-2-yl)heptanamide. b.p. 82° C/0.07 mm.

Analysis: $C_{13}H_{21}NO_2$ req.: C 69.9; H 9.48; N 6.27%. found: C 69.8; H 9.49; N 6.21%.

EXAMPLE 26

N-Hexyl-N-(5-methyl-fur-2-yl)heptanamide. b.p. 126° C/0.09 mm.

Analysis: $C_{18}H_{31}NO_2$ req.: C 73.7; H 10.7; N 4.77%. found: C 73.7; H 10.9; N 4.82%.

EXAMPLE 27

N-(5-Methyl-fur-2-yl)-N-(4-nitrobenzyl)heptanamide. b.p. 175° C/0.05 mm (Kugelrohr).

Analysis: $C_{19}H_{24}N_2O_4$ req.: C 66.3; H 7.02; N 8.14%. found: C 66.1; H 7.06; N 8.09%.

The above furans were additionally characterised by ir, uv and nmr spectra.

EXAMPLE 28

N-n-Butyl-N-(5-phenyl-fur-2-yl)-2-methylpropanamide.

tert-Butyl-5-phenyl-2-furylcarbamate, m.p. 87° C. prepared as in Example 1 from 5-phenyl-2-furoic acid was reacted as in Example 8 to give the title compound. b.p. 142° C/0.3 mm.

Analysis: $C_{18}H_{23}NO_2$ req.: C 75.7; H 8.12; N 4.91%. found: C 75.5; H 8.15; N 4.67%.

In a similar manner were prepared the following furans.

EXAMPLE 29

N-Methyl-N-(5-phenyl-fur-2-yl)cyclopentane carboxamide b.p. 140° C/0.07 mm.

Analysis: $C_{17}H_{19}NO_2$ req.: C 75.8; H 7.11; N 5.20%. found: C 76.1; H 7.33; N 5.36%.

EXAMPLE 30

N-n-Butyl-N-(5-phenyl-fur-2-yl)cyclopentane carboxamide b.p. 160° C/0.05 mm (Kugelrohr).

Analysis: $C_{20}H_{25}NO_2$ req.: C 77.1; H 8.09; N 4.50%. found: C 77.1; H 7.97; N 4.49%.

EXAMPLE 31

N-Benzyl-N-(5-phenyl-fur-2-yl)cyclopentane carboxamide. b.p. 180° C/0.04 mm (Kugelrohr).

Analysis: $C_{23}H_{23}NO_2$ req.: C 80.0; H 6.71; N 4.06%. found: C 79.8; H 6.45; N 4.05%.

EXAMPLE 32

N-n-Buryl-N-(5-phenyl-fur-2-yl)heptanamide b.p. 160°C/0.1 mm (Kugelrohr).

Analysis: $C_{21}H_{29}NO_2$ req.: C 77.0; H 8.93; N 4.28%. found : C 77.3; H 9.10; N 4.29%.

EXAMPLE 33

N-Allyl-N-(5-phenyl-fur-2-yl)heptanamide b.p. 145° C/0.15 mm (Kugelrohr).

Analysis: $C_{20}H_{25}NO_2$ req.: C 77.1; H 8.09; N 4.50%. found : C 77.4; H 7.85; N 4.40%.

EXAMPLE 34

N-n-Butyl-N-[5-(4-chlorophenyl)-fur-2-yl]-2-methylpropanamide b.p. 152° C/0.08 mm.

Analysis: $C_{18}H_{22}ClNO_2$ req.: C 67.6; H 6.93; N 4.38%. found: C67.5; H 7.17; N 4.33%.

EXAMPLE 35

N-n-Butyl-N-(fur-3-yl)-2-methyl propanamide tert-Butyl 3-furyl carbamate, m.p. 120° C. prepared as Example 1 from 3-furoic acid was reacted as in Example 2 to give N-(fur-3yl)-2-methyl propanamide, m.p. 122° C, which was then reacted as in Example 4 to give the desired N-n-butyl derivative b.p. 115° C/0.1 mm (Kugelrohr).

Analysis: $C_{12}H_{19}NO_2$ req.: C 68.9; H 9.15; N 6.69%. found: C 68.6; H 8.93; N 6.47%.

In a similar manner was prepared

EXAMPLE 36

N-n-Butyl-N-(fur-3-yl)cyclopentane carboxamide b.p. 105° C/0.15 mm (Kugelrohr).

Analysis: $C_{14}H_{21}NO_2$ req.: C 71.4; H 9.00; N 5.97%. found: C 71.2; H 9.23; N 5.76%.

EXAMPLE 37 tert-Butyl-(5-methyl-2-thienyl)carbamate

This was prepared using the procedure described in Example 1 except that 5-methyl-2-thiophenecarboxylic acid was used instead of 2-furoic acid. The carbamate was obtained as cream crystals, m.p. 86-89° C.

Analysis: $C_{10}H_{15}NO_2S$ req.: C 56.3; H 7.0; N 6.6%. found: C 56.4; H 7.25; N 6.6%.

EXAMPLE 38

N-(5-Methyl-2-thienyl)-2-methylpropanamide

The carbamate product of Example 37 was treated in an exactly analogous manner to that described in Example 2. The title compound was obtained as white plates, m.p. 95°–97° C.

Analysis: $C_9H_{13}NOS$ req.: C 59.0; H 7.1; N 7.65%. found: C 59.2; H 6.9; N, 7.7%.

EXAMPLE 39

N-(5-Methyl-2-thienyl)cyclopropylcarboxamide

This was prepared using the procedure of Example 38 and was obtained as buff crystals, m.p. 159°–161° C.

Analysis: $C_9H_{11}NOS$ req.: C 59.6; H 6.1; N 7.7%. found: C 59.5; H 6.1; N 7.85%.

EXAMPLE 40

N-(n-Butyl)-N-(5-methyl-2-thienyl)cyclopropyl carboxamide

This was prepared using the procedure of Example 2 and was obtained as a light yellow oil, b.p. 109° –110° C/0.7 mm.

Analysis: $C_{13}H_{19}NOS$ req.: C 65.8; H 8.0; N 5.9%. found: C 65.6; H 8.2; N 5.8%.

EXAMPLE 41

N-(3-Carbomethoxy-5-methyl-2-thienyl)cyclopropylcarboxamide

Cyclopropanecarboxylic acid chloride (10.9 g, 0.105 mol) was added dropwise during 40 min. to a stirred solution of methyl 2-amino-5-methyl3-thiophene-carboxylate (prepared by the method of Gewald, *Chemische Berichte*, 99, 94, (1966)), (17.1 g, 0.1 mol) in anhydrous pyridine (100 ml) kept at 0° C. The reaction mixture was stirred below 10° C for the next 4 hours, at room temperature overnight, and finally under reflux for 1.5 hours. The excess of pyridine was evaporated under reduced pressure and the residue was dissolved in $CHCl_3$ (200 ml) and extracted in turn with 2N-HCl, $H_2O$, 2N-NaOH and $H_2O$. The dried ($Na_2SO_4$) organic solution was evaporated and the residue was recrystallised from EtOH to yield the amide as yellow crystals (11.1 g, 46%), m.p. 121°–123° C.

Analysis: $C_{11}H_{13}NO_3S$ req.: C 55.2; H 5.4; N 5.85%. found: C55.3; H 5.3; N 5.7%.

EXAMPLE 42

N-(5-Methyl-2-thienyl)cyclopropylcarboxamide

A hot solution of the foregoing ester (14.8 g, 0.062 mol) in collidine (50 ml) was added to a hot solution of lithium iodide dihydrate (40.8 g, 0.24 mol) in collidine (80 ml) kept under nitrogen. The reaction was stirred under reflux for 48 hours, cooled, and equilibrated between diethyl ether (2 × 300 ml) and 4N-HCl (400 ml). The organic layer was washed successively with $H_2O$, 2N-NaOH and $H_2O$. Evaporation of the dried ($Na_2SO_4$) $Et_2O$ solution gave the required product as a cream solid, (7.3 g, 65%), m.p. 159-161° C.

Analysis: $C_9H_{11}NOS$ req.: C 59.6; H 6.1; N 7.7%. found: C 59.5; H 6.1; N 7.85%.

EXAMPLE 43

N-allyl-N-(5-methyl-2-thienyl)cyclopropylcarboxamide

A solution of the above amide (3.7 g, 0.0204 mol) in dry DMF (25 ml) was added during 30 min. to a stirred suspension of sodium hydride (0.49 g, 0.0204 mol) in dry DMF (50 ml). The dark reaction mixture was stirred at room temperature for a furthher 1.5 hours and allyl bromide (2.72 g) was added. The reaction was stirred at room temperature for 16 hours, and the DMF was evaporated under reduced pressure. The residue was equilibrated between $Et_2O$ (100 ml) and $H_2O$ (100 ml). The organic layer was washed with $H_2O$ (50ml), dried ($Na_2SO_4$) and distilled to give the required product as an almost colourless oil (3.1 g, 69%), b.p. 124°–127° C/0.6 mm.

Analysis: $C_{12}H_{15}NOS$ req.: C 65.15; H 6.8; N 6.3%. found: C 65.0 ; H 6.6; N 6.0%.

EXAMPLE 44

N-(p-Bromobenzyl)-N-(5-methyl-2-thienyl)cyclopropylcarboxamide

By the same method as that described in the previous example, this amide was obtained as a colourless oil (56%), b.p. 187°–191° C/0.45 mm. The oil solidified on cooling to give white crystals, m.p. 66°–69° C, which could be recrystallised from petroleum ether.

Analysis: $C_{16}H_{16}BrNOS$ req.: C 54.85; H 4.6; N 4.0%. found: C 54.6 ; H 4.8; N 4.2%.

EXAMPLE 45

N-n-Hexyl-N-(3-carbethoxy-5-ethyl-2-thienyl)-2-methylpropanamide

Ethyl 2-amino-5-ethyl-3-thiophenecarboxylate (*Chemische Berichte* 99, 94 (1966) )was converted into N-(3-carbethoxy-5-ethyl-2-thienyl)-2-methylpropanamide by the method described in Example 41. Alkylation of the unpurified product with n-hexyl iodide as described in Example 43 gave the title compound as a light yellow oil, b.p. 145°–147° C/0.25 mm. NMR showed that the material was the correct product.

EXAMPLE 46

5-Ethyl-2-(N-n-hexyl-2-methylpropanamido)-3-thiophenecarboxylic acid

A solution of potassium hydroxide (1.758 g) in water (10 ml) was added to a solution of the foregoing amide (11.1 g, 0.0314 mol) in ethanol (25 ml) and the reaction was kept at room temperature for 4 days. The solution was concentrated to quarter volume at 40° C and a large excess of 2N-HCl was added. The product was extracted with $CHCl_3$ to give a light yellow oil. This crystallised from petroleum ether (b.p. 60°–80° C) to yield the title compound as white crystals, m.p. 98°–101° C.

Analysis: $C_{17}H_{27}NO_3S$ req.: C 62.8; H 8.3; N 4.3%. found: C 62.7; H 8.0; N 4.2%.

EXAMPLE 47

N-n-Hexyl-N-(5-ethyl-2-thienyl)-2-methylpropanamide

The foregoing carboxylic acid (3.0 g) was heated at 200°–210° C for 25 min. The cooled reaction mixture was dissolved in $CHCl_3$ (25 ml) and washed in turn with 2N-NaOH (25 ml) and $H_2O$ (3 × 25 ml). The dried ($Na_2SO_4$) organic solution was evaporated and the residue was purified by preparative glc. Spectral data (including mass spectrum) confirmed the identity of the product.

EXAMPLE 48

N-(3-Carbomethoxy-5-methyl-2-thienyl)-2-methylpropanamide isoButyryl chloride (22.4 g) was added dropwise during 40 minutes to a stirred solution of methyl-2-amino-5-methyl-3-thiophenecarboxylate (34.2 g, 0.2 mol) in dry hexamethylphosphoramide (100 ml) kept at 5°–10° C. This temperature was maintained for a further 1 hour and then the reaction was kept at room temperature for 16 hours. The reaction mixture was poured into water (1600 ml) and the yellow precipitate was filtered off, washed with water and dried at 50° C. Recrystallisation of the solid from petroleum ether (b.p. 60°–80° C yielded cream crystals (39.6 g, 88%), m.p. 63°–65° C.

Analysis: $C_{11}H_{15}NO_3S$ req.: C 54.8; H 6.2; N 5.8%. found: C 54.9; H 6.4; N 6.1%.

EXAMPLE 49

N-(5-Methyl-2-methylpropanamide

The foregoing product was treated in the same way as described in Example 42 to give the title compound as a white solid (14.8 g, 54%), m.p. 96°–97° C.

Analysis: $C_9H_{13}NOS$ req.: C 59.0; H 7.1; N 7.65%. found: C 59.2; H 6.9; N 7.7%.

EXAMPLE 50

N-Benzyl-N-(5-methyl-2-thienyl)-2-methylpropanamide

By the method described in Example 43, the foregoing product was converted into the title compound which was obtained as a light yellow oil (4.15 g, 61%), b.p. 132°–134° C/0.3 mm.

Analysis: $C_{16}H_{19}NOS$ req.: C 70.3; H 6.95; N 5.1%. found: C 70.1; H 7.1; N 5.2%.

EXAMPLE 51

N-n-Hexyl-N-(5-methyl-2-thienyl)-2-methylpropanamide

By the method described in Example 43, N-(5-methyl-2-thienyl)-2-methylpropanamide gave the title compound as an almost colourless oil (4.1 g, 71%), b.p. 109°–111° C/0.35 mm.

EXAMPLE 52

N-(3-Carboxymethyl-5-phenyl-2-thienyl)-benzamide

Methyl 2-amino-5-phenyl-thiophene-3-carboxylate (1.3 g, 0.0055 mole) in hexamethyl phosphoramide (prepared by the method of *Chemische Berichte,* 99, 94 (1966) but using methyl cyanoacetate in place of ethyl cyanoacetate) (20 ml.) was stirred and treated with benzoyl chloride (1.56 g, 1.28 ml, 0.011 mole). The solution was stirred for 2 hours, poured into water (750 ml), stored overnight and the title compound filtered off (1.31 g) m.p. 190° C. Similarly prepared was: N-(3-Carboxymethyl-5-phenyl-2-thienyl) cyclohexane carboxamide, m.p. 121°–122° C.

EXAMPLE 53

N-(5-Phenyl-2-thienyl)-benzamide a. Lithium iodide dihydrate (25.5 g, 0.168 mole) in collidine (50 ml) under nitrogen were stirred and refluxed until the LiI dissolved. The amido-ester of Example 52 (17 g, 0.053 mole) in ward collidine (400 ml) was added and the solution stirred and refluxed for 48 hours. The cooled solution was poured into a mixture of 5N. HCl (800 ml., 4 mole) and ice, extracted with chloroform, which was washed with saturated sodium hydrogen carbonate solution, dried ($Na_2SO_4$), and evaporated to leave a semisolid. This was heated in vacuo with water to remove residual collidine, stirred with saturated sodium hydrogen carbonate solution, the solid filtered, washed with water and dried to give the title compound (7.85 g) (m.p. 202°–203° C.).

b. The title compound was also prepared from 2-amino-5-phenylthiophene hydrochloride (2.1 g, 0.01 mole) which was dissolved in hexamethyl phosphoramide (20 ml) under nitrogen, treated with triethylamine to liberate the amine, and then with benzoyl chloride (2.1 g, 0.015 mole, 1.73 ml), stirred 1.5 hours, and poured into water (400 ml.) to give the title amide (1.52 g) (m.p. 202°–203° C.) after recrystallisation from EtOH, as yelloww micro-rectangular platelets.

EXAMPLE 54

N-(5-Phenyl-2-thienyl)cyclohexane carboxamide

This compound (m.p. 174° C.) was prepared from N-(3-carboxy-methyl-5-phenyl-2-thienyl)-cyclohexane carboxamide (31.1 g, 0.1 mole) and LiI. $2H_2O$ (48.1 g, 0.32 mole) by refluxing in collidine (125 ml.) according to the procedure of Example 53 (a). This compound was also prepared according to the procedure of Example 53(b), using cyclohexane carboxylic acid as the acylating agent. The products of the two processes were spectrally identical and had a melting point of 175° C.

EXAMPLE 55

N-p-Chlorobenzyl-N-(5-phenyl-2-thienyl)-benzamide

The amide of Example 53 (2.8 g, 0.01 mole) in dimethylformamide (25 ml.) was added to sodium hydride (0.0105 mole) (from 40–50% NaH in oil, 0.74 g) which was stirred in dimethylformamide (25 ml.) and cooled in ice. The mixture was stirred for 0.5 hr. and treated with a solution of p-chlorobenzyl chloride (3.22 g, 0.02 mole) in DMF (15 ml.) and a trace of NaI. The mixture was stirred, initially at ice-bath temperature and then at room temperature overnight and then refluxed for 3 hours to complete the reaction. The DMF was evaporated off, water was added, the product extracted with chloroform, which was dried ($Na_2SO_4$), filtered and evaporated to give the N-p-chlorobenzyl-benzamide (2.07 g.) as a viscous oil, b.p. 240°–245° C./0.35 mm.Hg. Mass spec. m/e 403.

EXAMPLES 56–69

Similarly, using the process described in Example 55 were prepared:

N-Butyl-N-(5-phenyl-2-thienyl)benzamide
  Viscous oil b.p. 232°–234° C./0.25 mm.$\eta_D^{21}$ 1.6338. Mass Spec. m/e 335.

N-Allyl-N-(5-phenyl-2-thienyl)cyclohexane carboxamide
  Oil, b.p. 178°–180° C./0.3 mm., $\eta_D^{22}$ 1.6028. Mass Spec. m/e 325.

N-Methyl-N-(5-phenyl-2-thienyl)cyclohexane carboxamide
  (m.p. 113°–114° C.).

N-Methyl-N-(5-phenyl-2-thienyl)benzamide
  (m.p. 128° C.)

EXAMPLES 70–72

Also prepared in a manner similar to Examples 29 to 34 were the following furans:

N-n-Butyl-N-[5-(3-trifluoromethylphenyl)fur-2-yl]-2-methylpropanamide b.p. 135° C./0.15 mm. (Kugelrohr).
  Analysis: $C_{19}H_{22}F_3NO_2$ req: C 64.6; H 6.28; N 3.96%. found: C 64.5; H 6.13; N 3.82%.

N-Methyl-N-[5-(3-trifluoromethylphenyl)-fur-2-yl]-2-methylpropanamide m.p. 68° C.

N-n-Butyl-N-[5-(4-methoxyphenyl)-fur-2-yl]-2-methylpropanamide b.p. 160° C./0.15 mm (Kugelrohr).
  Analysis: $C_{15}H_{25}NO_2$ req: C 71.7; H 10.0; N 5.57%. found: C 71.9; H 9.83; N 5.30%.

EXAMPLES 73 and 74

The following furans were prepared in similar manner to Example 35:

N-n-Butyl-N-(fur-3-yl)-heptanamide b.p. 110° C/0.15 mm. (Kugelrohr).

Analysis: $C_{15}h_{25}NO_2$ req: C 71.7; H 10.0; N 5.57% found: C 71.9; H 9.83; n 5.30%

N-Methyl-N-(fur-3-yl)-heptanamide b.p. 95°–100° C/0.15 mm (Kugelrohr).

Analysis: $C_{12}H_{19}NO_2$ req: C 68.9; H 9.15; N 6.69%. found: C 69.1; H 9.05; N 6.49%.

EXAMPLE 75

N-(5-Methyl-2-thienyl)-2-methylpropanamide

N-(3-Carbomethoxy-5-methyl-2-thienyl)-2-methylpropanamide (4.1 g, 0.017 mol), prepared by the method of Example 48, was dissolved in hot collidine (10 ml) and added to a mixture of lithium iodide dihydrate (10.1 g, 0.06 mol) in collidine (20 ml) kept under nitrogen. The reaction mixture was stirred under reflux for 48 hours, cooled and equilibrated between ether (3 × 50 ml) and 5N-hydrochloric acid (50 ml). The ethereal solution was washed with water (25 ml), dried ($Na_2SO_4$) and evaporated to yield the required product as an off-white solid (2.7 g, 47%) m.p. 96°–97° C. The product was identical to the product described in Example 38.

EXAMPLE 76

N-n-Butyl-N-(5-methyl-2-thienyl)-2-methylpropanamide

The product of Example 75 was alkylated as in Example 2 to give the required product, which was in the form of an almost colourless oil (4.1 g, 71%), b.p. 116°–119° C./0.6 mm., $\eta_D^{19}$ 1.5075.

EXAMPLE 77

5-Methyl-2-(2-methylpropanamido)-3-thiophenecarboxylic acid

The ester from Example 48 was treated with lithium iodide dihydrate as in Example 42 to give the expected decarboxylated product, N-(5-methyl-2-thienyl)-2-methylpropanamide, m.p. 96°–97° C. in 54% yield.

The caustic aqueous extracts were acidified with concentrated hydrochloric acid to yield a precipitate. This was filtered off, washed with water and recrystallised from aqueous ethanol to yield the title compound as white needles (23%), m.p. 160°–162° C.

EXAMPLE 78

N-(3-Carbomethoxy-5-methyl-2-thienyl)-phenylacetamide

The process of Example 48 was carried out using phenylacetyl chloride instead of isobutyryl chloride. The required product was obtained as a solid (98%) m.p. 107°–109° C.

EXAMPLE 79

N-(5-Methyl-2-thienyl)phenylacetamide

The product of Example 78 was treated with lithium iodide dihydrate as in Example 42. The title compound was obtained as cream needles (75%), m.p. 127°–129° C. from methanol-petroleum ether (b.p. 60°–80° C).

EXAMPLE 80

N-Methyl-N-(5-methyl-2-thienyl)phenylacetamide

The product of Example 79 was alkylated with iodomethane as in Example 2 to yield the required product (59%) m.p, 77°–79° C. from cyclohexane.

EXAMPLE 81

N-Allyl-N-(5-methyl-2-thienyl)phenylacetamide

N-(5-Methyl-2-thienyl)phenylacetamide produced as in Example 79 was alkylated with allyl bromide as in Example 2. The required product was obtained as a light red oil (63%), b.p, 144°–145° C./0.25 mm, $\eta_D^{20}$ 1.5742.

The following Examples 82 to 86 illustrate pharmaceutical formulations containing the active compound N-n-butyl-N-(5-phenyl-2-thienyl)-benzamide.

EXAMPLE 82

Soft gelatin capsules were prepared using the following ingredients:

|  | Quantity (mg/capsule) |
|---|---|
| Active compound | 30 |
| Propyl gallate | 0.02 |
| Fractionated Coconut Oil B.P.C. | 70 |
|  | 100.02 |

The above ingredients were mixed and filled into soft gelatin capsules, the main shell components of which were gelatin and glycerine.

EXAMPLE 83

Hard gelatin capsules were prepared using the following ingredients:

|  | Quantity (mg/capsule) |
|---|---|
| Active compound | 30 |
| Silicon dioxide (fumed) | 25 |
| Lactose | 45 |
| Butylated hydroxyanisole B.P. | 0.02 |

The butylated hydroxyanisole was issolved in the active ingredient and the solution so formed adsorbed onto the silicon dioxide (fumed). The lactose was then added and the whole mixed. Finally, the mixture was filled into hard gelatin capsules.

EXAMPLE 84

Suppositories containing 30 and 60 mg. of the comound are prepared as follows:

| Active compound | 3 g. |
|---|---|
| Henkel base | 97 g. |

The active compound is mixed with the Henkel base which had been previously melted using the minimum amount of heat possible. The mixture is then poured into suppository moulds of a nominal capacity of 1 g, or 2 g, as desired, to produce suppositories each containing 30 mg. or 60 mg. of the active compound.

EXAMPLE 85

An aerosol was prepared containing the following ingredients:

|  | Quantity per ml. |
|---|---|
| Active compound | 15 mg. |
| Propylene glycol | 15 mg. |
| Dichlorotetrafluoroethane (Propellant 114) | 600 mg. |
| Dichlorodifluoromethane | 850 mg. |

| (Propellant 12) | Quantity per ml. |
|---|---|

The active compound is mixed with the propylene glycol and the mix added to the propellant 114, the mixture cooled to −15° to −20° C. and transferred to a filling device. At the same time a mixture of propellants 114 and 12, previously cooled to −15° to −20° C. is fed into a second filling device. A metered amount of propellant from the second filling device is introduced into a stainless steel container, followed by the required amount of material from the first filling device. The valve units are then fitted and sealed to the container. These valve units may be equipped with metering device so that approximately 0.20 mg. of the active compound is released by a single actuation of the valve.

EXAMPLE 86

Tablets were prepared using the following components:

| Active compound | 15.00 mg. |
|---|---|
| Microcrystalline Cellulose | 250.00 mg. |
| Sodium Carboxymethyl Starch | 20.00 mg. |
| Magnesium Stearate | 3.00 mg. |
| Butylated Hydroxyanisole B.P. | 0.002 mg. |

The hydroxyanisole was dissolved in the active compound, the solution adsorbed onto the microcrystalline starch. This was mixed with the sodium carboxymethyl starch and then the magnesium stearate was mixed in. Finally, the mixture was compressed to form tablets.

In the foregoing Examples 82 to 86 the liquid active compound used may, in accordance with the invention, be replaced wholly or in part by other liquid active compounds of formula (I). If the active compound is a solid, appropriate modification will of course have to be made.

We claim:

1. A compound of formula (I):

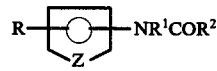

wherein Z represents sulphur; R is hydrogen, or $C_{1-4}$ alkyl; $R^1$ is $C_{1-7}$ alkyl, $C_{3-6}$ alkenyl, or $C_{3-6}$ alkynyl and $R^2$ is $C_{3-10}$ cycloalkyl.

2. A compound of formula (I) according to claim 1, wherein the acylamino group -$NR^1COR^2$ is present at the 2- or 3- position of the thienyl nucleus and wherein R is a substituent at the 5-position of said nucleus.

3. A compound of Formula (I) according to claim 1, wherein R is hydrogen or a $C_1$-$C_4$ alkyl substituent at the 5- position of the thienyl nucleus; $R^2$ is $C_{3-5}$ cycloalkyl and the acylamino group —$NR^1COR^2$ is present at the 2- or 3- position of the thienyl nucleus.

4. A compound according to claim 1 being N-allyl-N-(5-methyl-2-thienyl)cyclopropylcarboxamide.

* * * * *